United States Patent
Spina et al.

(10) Patent No.: US 12,084,550 B2
(45) Date of Patent: Sep. 10, 2024

(54) VEHICLES AND DELIVERY SYSTEMS FOR OXIDIZING AGENTS

(71) Applicant: EXCITON PHARMA CORP., Toronto (CA)

(72) Inventors: Carla Jehan Catherine Spina, Toronto (CA); Johanny Elizabeth Notarandrea Alfonzo, Toronto (CA)

(73) Assignee: EXCITON PHARMA CORP. (CA)

( * ) Notice: Subject to any disclaimer, the term of this patent is extended or adjusted under 35 U.S.C. 154(b) by 765 days.

(21) Appl. No.: 17/252,640

(22) PCT Filed: Jul. 26, 2018

(86) PCT No.: PCT/CA2018/050907
§ 371 (c)(1),
(2) Date: Dec. 15, 2020

(87) PCT Pub. No.: WO2020/019050
PCT Pub. Date: Jan. 30, 2020

(65) Prior Publication Data
US 2021/0253804 A1    Aug. 19, 2021

(51) Int. Cl.
| | |
|---|---|
| *C08J 3/22* | (2006.01) |
| *C08K 3/22* | (2006.01) |
| *C08K 3/28* | (2006.01) |
| *C08K 3/36* | (2006.01) |
| *B82Y 30/00* | (2011.01) |
| *B82Y 40/00* | (2011.01) |

(52) U.S. Cl.
CPC ............... *C08J 3/226* (2013.01); *C08K 3/22* (2013.01); *C08K 3/28* (2013.01); *C08K 3/36* (2013.01); *B82Y 30/00* (2013.01); *B82Y 40/00* (2013.01); *C08J 2383/04* (2013.01); *C08K 2003/2241* (2013.01); *C08K 2201/011* (2013.01)

(58) Field of Classification Search
CPC ..... C08J 3/22; C08K 3/22; C08K 3/36; C08K 3/28
USPC .......................................................... 523/351
See application file for complete search history.

(56) References Cited

U.S. PATENT DOCUMENTS

| | | | |
|---|---|---|---|
| 6,613,311 B2 | 9/2003 | Imperial | |
| 8,263,114 B2 | 9/2012 | Berlat | |
| 2002/0141954 A1* | 10/2002 | Imperial | A61Q 5/08 424/62 |
| 2013/0042883 A1* | 2/2013 | DeGeorge | A61K 8/23 424/62 |

FOREIGN PATENT DOCUMENTS

| | | |
|---|---|---|
| CA | 2460585 | 11/2004 |
| WO | 2011129759 | 10/2011 |
| WO | 2018027318 | 2/2018 |

OTHER PUBLICATIONS

Djokic, Deposition of Silver Oxysalts and Their Antimicrobial Properties, Journal of the Electrochemical Society, 151 (6) C359-C364 (2004).
Lemire et al, Silver Oxynitrate, an Unexplored Silver Compound with Antimicrobial and Antibiiofilm Activity, Antimicrobial Agents and Chemotherapy, vol. 59, No. 7, pp. 4031-4039, Jul. 2015.
Kalan et al, Targeting biofilms of multidurg-resistant bacteria with silver oxynitrate, International Journal of Antimicrobial Agents, 49, 719-726 (2017).

\* cited by examiner

*Primary Examiner* — Deve V Hall
(74) *Attorney, Agent, or Firm* — Kirsten M. Oates; Rodman & Rodman LLP (57) ABSTRACT

Compositions include a hydrophobic continuous phase having a powdery oxidizing agent (e.g. silver oxynitrate) and a disperse hydrophilic phase comprising at least one hydrophilic substance (e.g. fumed silica) that maintain antimicrobial/anti-biofilm activities; and methods for preparing and using same.

38 Claims, 5 Drawing Sheets

VEHICLES AND DELIVERY SYSTEMS FOR OXIDIZING AGENTS

FIELD OF THE INVENTION

A composition comprising a hydrophobic continuous phase, a disperse hydrophilic phase, and an oxidizing agent; and methods for preparing and using same.

BACKGROUND OF THE INVENTION

Semi-solid compositions such as lotions, creams, pastes, gels, and ointments are abundant in foods, pharmaceuticals, and personal care products. Lotions are oil-in-water emulsions with or without alcohol and often emollients. Similarly, creams are emulsions of oil in water in approximately equal proportions but are more viscous than lotions. Pastes are combinations of solid-state powders and liquid media inclusive of oil or water. Gels are dilute cross-linked systems exhibiting no flow in the steady state with a range of apparent viscosities and may liquefy at body temperature. Ointments are homogeneous preparations of high viscosity oils, and often emollients. Physical or textural properties of these compositions are achieved through the inclusion of rheological modifiers, emulsifiers, thickening agents, surfactants, and variation of oil/water phase ratios. Inclusion of active agents often requires the use of stabilizers and preservatives to provide desirable rheology and to prevent undesirable oxidation (Trumbore et al. 2017).

In semi-solid compositions containing an aqueous phase such as lotions and creams, water or air-sensitive active agents are masked or encapsulated using surfactants to confer stability, thereby preserving their structure and activity over the lifespan of the composition (Lapidot et al. 2013; Betageri 2014; Neoh et al. 2007; Arora et al. 2012). The surfactants create barriers around the active agents, facilitating regulated release while shielding against air or aqueous-induced degradation. Antioxidants or preservatives prevent undesirable oxidation and degradation of active agents (U.S. Pat. No. 9,962,339 to Karp et al.). However, these strategies are disadvantageous due to the presupposition and commonality that active agents are sensitive to oxidation. In the case of oxidizing agents, having a reduction potential greater than 0.0 V versus a standard hydrogen electrode (SHE) and exhibiting a greater tendency to gain electrons rather than lose electrons, these strategies for stabilization are detrimental to the preservation of their activity and composition. Formulations of oxidizing agents in oil-in-water emulsions have included fluorinated copolymers but are undesirable due to the biocompatibility of fluorinated polymers and functionalization limitations with other metal oxides (Zenerino et al. 2015). Chemical oxidation of preservatives and surfactants by oxidizing agents, such as silver oxynitrate, results in composition instability and inactivation of operational ingredients. As such, classical composition strategies have not been applied to oxidizing agents or ingredients.

Alternate strategies involve use of antibiotic or antimicrobial zeolites as carriers for active agents. In U.S. Pat. No. 8,021,683, Berlat describes a composition including a non-volatile silicone fluid in admixture with fumed silica, a volatile diluent, a silicone elastomer, and an active agent which may be an antibiotic zeolite in which ion-exchangeable ions in the zeolite are partially or completely ion-exchanged with antibiotic ions including silver ions. During preparation of the composition, the fumed silica is mixed at the onset with the non-volatile silicone fluid, volatile diluent, and silicone elastomer to form a masterbatch which is subsequently blended with a prepared antibiotic zeolite to produce the final composition in the form of a gel. In use, the zeolite absorbs water and an ion exchange occurs between sodium ions contained in the water and silver ions which are bound to the zeolite in order to provide a controlled release of silver ions. Similarly, in U.S. Pat. No. 4,938,958, Niira et al. describe an antibiotic resin composition containing a resin and an antibiotic zeolite in which all or a portion of ion-exchangeable ions in the zeolite are replaced with antibiotic metal ions and ammonium ions to prevent the leaching out of the antibiotic metal ions from the zeolite carrier. However, the antibiotic metal ions may be susceptible to degradation during preparation of the composition since a prepared aqueous mixed solution containing the antibiotic metal ions and ammonium ions is contacted with a zeolite to cause ion-exchange between the ions in the zeolite and the aforesaid ions.

Alternate strategies include incorporation of active agents into non-aqueous systems such as gels, pastes, or ointments. The use of surfactants or water-soluble non-aqueous phases may facilitate the release of the active agents, or diffusion of the active agents from the non-aqueous composition to an external water phase, upon contact with an aqueous interface. In U.S. Pat. No. 8,486,374, Tamarkin et al. describe the incorporation of active agents, antioxidants, and surfactants into polyalkyl glycols base compositions. These strategies are advantageous for active agents subject to degradation by oxygen or air, stabilizing the active agents while conferring release of active agents from the composition into the desired target. However, in the case of oxidizing agents, their positive reduction potential results in degradation of the glycol base, surfactants, and preservatives, destabilizing the composition. These strategies are thus non-conducive to compositions incorporating oxidizing agents.

Alternate strategies involve use of non-aqueous bases to increase the stability of water-sensitive active agents. Such compositions include glycerides (Chen 2004), polyalcohols (Borja et al. 2017), organic solvents and alcohols (Doxey et al. 2016), or fatty alcohols (U.S. Pat. No. 9,161,916 to Tamarkin et al.) as continuous media. Silicone oils, mineral oils, or vegetable oil confer increased stability to active agents (U.S. Pat. No. 9,226,890 to Lamberty & Lin). Inherently hydrophobic, these compositions are beneficial in stabilizing water and air-sensitive active agents, although they are generally poor solvents and usually decrease the drug delivery capabilities of the system, therefore requiring inclusion of hydrophilic carriers, surfactants, emollients, antioxidants, and viscosity modifiers to allot desired composition characteristics and release of active agents into aqueous media (U.S. Pat. No. 9,050,253 to Tamarkin et al.). Eliminating aqueous components from the final compositions and incorporating anti-oxidants and surfactants may stabilize or prevent undesirable oxidation of active agents and facilitate release into aqueous media. However, where the active agents are oxidized materials and exhibit a positive reduction potential, the non-aqueous organic media, antioxidants, and surfactants are subject to undesirable oxidation and degradation, resulting in destabilization of the composition and undesirable reactivity and degradation with the higher oxidation state materials. As such, conventional non-aqueous compositions are unsuitable for compositions containing oxidizing agents.

SUMMARY OF THE INVENTION

The present invention relates to a composition comprising a hydrophobic continuous phase, a disperse hydrophilic phase, and an oxidizing agent. The composition may optionally comprise one or more excipients. The composition may be a semi-solid composition. Further, the invention relates to methods of preparing and using the composition.

Broadly stated, in one aspect, the invention comprises a composition comprising: a hydrophobic continuous phase comprising an oxidizing agent; and a disperse hydrophilic phase comprising at least one hydrophilic substance.

The composition comprises a hydrophobic continuous phase within which the oxidizing agent is suspended or dispersed such that the water-repelling property of the hydrophobic continuous phase may shield the oxidizing agent against water-induced degradation. In some embodiments, the hydrophobic continuous phase may comprise less than about 5 wt/wt % water, and exhibit an initial viscosity ranging from about 0 centipoise to about 1000 centipoise. In some embodiments, the hydrophobic continuous phase may comprise a polymeric compound including, but not limited to, an aliphatic or silicone based short chain, or a polymeric compound including, but not limited to, a lower alkane, higher alkane, liquid paraffin, paraffin wax, petrolatum, polydimethylsiloxane, polyalkylsiloxane, a dialkylsiloxane polymer, a dialkylsiloxane polymer comprising one or more polydimethylsiloxanes, or a combination thereof. In some embodiments, the polymeric compound may comprise polydimethylsiloxane exhibiting a viscosity ranging from about 5 centipoise to about 1,000 centipoise, and in an amount ranging from about 35 wt/wt % to about 80 wt/wt %. In some embodiments, the hydrophobic continuous phase may further comprise a non-aqueous solvent including, but not limited to, dimethylsulfoxide, dichloromethane, tetrahydrofuran, and chloroform. In some embodiments, a secondary or ternary non-aqueous base may be included in an amount ranging from about 1.0 wt/wt % to about 90 wt/wt %.

The composition further comprises a disperse hydrophilic phase comprising at least one hydrophilic substance. In some embodiments, the disperse hydrophilic phase may comprise nanostructured silica including, but not limited to, nano silica, fumed silica, or a combination thereof. The amount of nanostructured silica may range from about 0.1 wt/wt % to about 30 wt/wt %. The ratio of fumed silica to nano silica may range from 1:0 to 0:1, and preferably from 1:0 to 1:3.

The composition further comprises an oxidizing agent which may exhibit various properties including oxidizing effects and therapeutic activity, such as antimicrobial, anti-inflammatory, antiseptic, antifungal, antiviral, or other activity.

In some embodiments, the oxidizing agent may comprise, consist of, or consist essentially of a transition, lanthanide, or actinide metal having at least one metal element in an oxidized state greater than a metallic state. The metal element may comprise silver, gold, copper, tin, titanium, zinc, iron, manganese, cobalt, platinum, nickel, cerium, or a combination thereof.

In some embodiments, the oxidizing agent may comprise, consist of, or consist essentially of metal complexes of tellurates, periodates, peroxides, perchlorates, permanganates, persulfates, phosphates, borates, carbonates, arsenates, or combinations thereof. In some embodiments in which the metal element is silver, the silver may be in the form of Ag(II) or Ag(III) oxidation state or a combination thereof. In some embodiments, the silver (II) or (III) complexes may be selected from silver fluoride, silver bipyridine, silver carbamate, silver pyridinecarboxylic acid, a silver porphyrin, silver biguanide, a silver oxide including AgO, $Ag_2O_2$, $Ag_4O_4$, $Ag_2O_3$, $Ag_3O_4$, $Ag_7O_8X$, wherein X comprises $HCO_3^-$, $BF_4^-$, $CO_3^{2-}$, $NO_3^-$, $ClO_4^-$, $SO_4^{2-}$, or $F^-$, or a combination thereof. In some embodiments, the silver may comprise silver oxynitrate $Ag_7NO_{11}$.

In some embodiments, the oxidizing agent may comprise, consist of, or consist essentially of a metal, metal oxide or metal fluoride with or without counterions including, but not limited to, a nitrate, carbonate, phosphate, sulfate, chloride, fluoride, perchlorate, tellurate, periodate, peroxide, permanganate, persulfate, borate, arsenate, or combinations thereof.

In some embodiments, the oxidizing agent may comprise, consist of, or consist essentially of a metal compound capable of forming bonds with a donor ligand including, but not limited to, dithiocarbamate, aliphatic dithioloate, aromatic dithioloate, selenium ligand, sulfur ligand, ethylenediaminetetraacetic acid, imine ligand, oxime ligand, dimethylglyoxime, macrocylic amine, porphyrin, tetraazacyclohexadiene, pyridine, pyrazine, bipyridyl, phenanthroline, dimethylphosphine, dimethylarsine, dibutylthiourea, ethylenediimine, polypeptide, guanide, biguanide, polyguanide, phosphine, arsine, or a combination thereof.

In some embodiments, the oxidizing agent may comprise, consist of, or consist essentially of a metalloid. As used herein, the term "metalloid" refers to an element whose properties are intermediate between those of metals and solid non-metals. Suitable metalloids include, but are not limited to, boron, borates, and borane, which exhibit antiseptic, antifungal, and antiviral properties against various protozoans responsible for tropical diseases.

In some embodiments, the oxidizing agent may comprise, consist of, or consist essentially of a polyatomic non-metal. As used herein, the term "polyatomic non-metal" refers to an element which lacks metallic attributes and contains more than one atom. Suitable polyatomic non-metals include, but are not limited to, tellurates, periodates, peroxides, perchlorates, permanganates, persulfates, selenium and graphene or higher order carbon nanostructures. Selenium increases immunity, defends against free radical damage and inflammation, and is present in several proteins that play a critical role in maintaining cellular redox homeostasis. Graphene or higher order carbon nanostructures are strongly hydrophobic, where oxidized graphene acts as a peroxidase-like mimetic.

The concentration of the oxidizing agent may range from about 0.1 wt/wt % to about 50 wt/wt %.

The composition may also comprise one or more excipients including, but not limited to, a Pickering agent, a surface-active agent, a hygroscopic agent, a hydrogeling agent, an opacifying agent, or a masking agent.

The Pickering agent may stabilize droplets against coalescence, and confer optical characteristics, and textural or physical properties to the composition. In some embodiments, the Pickering agent includes, but is not limited to, a mineral, a clay, chitosan, cyclodextrin, starch, alginate, cellulose, or a combination thereof. The amount of the Pickering agent may range from about 0.1 wt/wt % to greater than about 15.0 wt/wt %.

The surface-active agent may lower the surface tension of the composition in which it is dissolved. In some embodiments, the surface-active agent includes, but is not limited to, an alkyl sulfonate, alkyl quaternary ammonium, imide, imine, or a block co-polymer of an alkane, alkylsiloxane, ethylene glycol, vinyl pyrrolidone, vinyl alcohol, acrylic acid, phosphate, polyethylene glycol/polypropylene glycol dimethicone, cetyltrimethylammonium, or a combination thereof. In some embodiments the amount of surface-active agent may range from about 0.1 wt/wt % to about 10.0 wt/wt %.

The hydrogeling agent may absorb or retain water or other aqueous solvents. In some embodiments, the hydrogeling agent includes, but is not limited to, a polymeric carbohydrate, saccharide, cellulose, acid, alcohol, pyrrolidone, bentonite, carbopol, carrageenan, xanthan gum, or a combination thereof. In some embodiments, the hydrogeling agent may comprise a water concentration of less than about 8.0 wt/wt %. In some embodiments, the amount of the hydrogeling agent may range from about 0.1 wt/wt % to about 10.0 wt/wt %.

The hygroscopic agent may attract and absorb water molecules from the surrounding environment. In some embodiments, the hydrogeling agent includes, but is not limited to, vegetal fibers (e.g., cellulose), sugar, glycerol, ethanol, methanol, and salts including sodium carbonate, calcium chloride, magnesium sulfate, and bases such as sodium hydroxide). In some embodiments, the hygroscopic agents include, but are not limited to, sulfate salts including magnesium, sodium and potassium, methylated cellulose, polyacrylates such as polyacrylic acid and salts thereof, and silica gel.

The opacifying agent may alter the tone or shade of the composition. In some embodiments, the opacifying agent includes, but is not limited to, titanium dioxide, zinc sulfate, zirconium oxide, zinc oxide, dolomite, barium sulfate, calcium carbonate, talc, or mica. The amount of the opacifying agent may range from about 1.0 wt/wt % to about 10 wt/wt %.

The masking agent may alter the perceived color of the composition. In some embodiments, the masking agent includes, but is not limited to, carbon black, pyrophyllite, alumina, aluminum, or bismuth oxychloride. The amount of the masking agent may range from about 1.0 wt/wt % to about 10 wt/wt %.

The composition may be prepared by selecting particular components and proportions based on the desired characteristics of the composition. In preparing the mixture, the composition may be formed by mixing the components in any order. In some embodiments, a method for preparing the composition comprises the steps of mixing the hydrophobic continuous phase and the oxidizing agent to form a mixture; and adding the disperse hydrophilic phase in portions to the mixture to form the composition. In some embodiments, the method may further comprise mixing one or more excipients including, but not limited to, a Pickering agent, a surface-active agent, a hydrogeling agent, a hygroscopic agent, an opacifying agent, or a masking agent.

In some embodiments, one or more components may be mixed in the following sequence: the hydrophobic continuous phase, one or more of an opacifying agent, masking agent, hydrogeling agent, surface-active agent, the oxidizing agent, and the disperse hydrophilic phase. In some embodiments, the components may comprise siloxane, titanium dioxide, aluminum powder, carboxymethyl cellulose, polyethylene glycol/polypropylene glycol (PEG/PPG) dimethicone, silver oxynitrate, and nanostructured silica. The method may be conducted at ambient temperature ranging from 0° C. to 60° C., preferably from 10° C. to 20° C. The components may be mixed at 2000 RPM for about 5 minutes per component.

In yet another aspect, the invention comprises use of the above compositions in the form of a semi-solid composition exhibiting antimicrobial or anti-inflammatory activity.

Without being bound by any theory, it is believed that the oxidizing agent is suspended or dispersed within the hydrophobic continuous phase such that the water-repelling property of the hydrophobic continuous phase may shield the oxidizing agent against air, light, thermal, or water-induced degradation. The disperse hydrophilic phase attracts water. In some embodiments, the property of a high surface area to volume ratio of nanostructured silica as the disperse hydrophilic phase may provide a greater potential for attracting water. When the semi-solid composition is exposed to water, the water may be attracted into the semi-solid composition by the disperse hydrophilic phase, thereby exposing the oxidizing agent to the water. As a result, the oxidizing agent may gradually dissolve and diffuse into the water, releasing the oxidizing agent gradually into the environment in which the semi-solid composition has been placed.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Embodiments of the Invention Will Now be Described with Reference to the Accompanying Drawings, in which.

DETAILED DESCRIPTION OF PREFERRED EMBODIMENTS

Unless defined otherwise in this specification, all technical and scientific terms are used herein according to their conventional definitions as they are commonly used and understood by those of ordinary skill in the art of synthetic chemistry, pharmacology and cosmetology.

The present invention relates to a semi-solid composition comprising a hydrophobic continuous phase, a disperse hydrophilic phase, and an oxidizing agent. In some embodiments, the composition may optionally comprise one or more excipients. In some embodiments, the composition may be formulated for topical application to the skin. All components of the composition are further described. In addition, the invention relates to methods of preparing and using the composition.

Hydrophobic Continuous Phase

The composition comprises a hydrophobic continuous phase. As used herein, the term "hydrophobic" means a physical property of repelling water. As used herein, the term "continuous phase" means an external phase in which a solid is suspended or liquid is dispersed. As used herein, the term "hydrophobic continuous phase" means a hydrophobic external phase having the physical property of repelling water, and in which a solid is suspended or liquid is dispersed. Preferably, the hydrophobic continuous phase contains less than about 5 wt/wt % water, and more preferably, less than about 2 wt/wt % water. The oxidizing agent is suspended or dispersed within the hydrophobic continuous phase such that the water-repelling property of the hydrophobic continuous phase may shield the oxidizing agent against water-induced degradation.

In certain embodiments, the hydrophobic continuous phase is preferentially liquid or semi-solid at room temperature. As used herein, the term "semi-solid" means a mechano-physical state of a material that is flowable under moderate stress. The property of being semi-solid may ease application or transfer of the composition on the skin or a surface (for example, a dressing) or in processing. Preferably, the hydrophobic continuous phase has an initial viscosity ranging from about 0 centipoise to about 1000 centipoise, and more preferably, from about 5 centipoise to about 50 centipoise.

In some embodiments, the hydrophobic continuous phase may comprise a polymeric compound. The polymeric compound includes, but is not limited to, an aliphatic or silicone based short chain, or polymeric compound including, but not limited to, a lower alkane ($C_5$ to $C_9$), higher alkane ($C_9$ to $C_{16}$), liquid paraffin, paraffin wax ($C_{20}$ to $C_{40}$), petrolatum, polydimethylsiloxane (PDMS), polyalkylsiloxane, a dialkylsiloxane, polymer, a dialkylsiloxane polymer comprising one or more polydimethylsiloxanes, or a combination thereof. More preferably, the hydrophobic continuous phase comprises dialkylsiloxane polymers, and most preferably, PDMS. PDMS has a viscosity ranging from about 5 to about 1,000 centipoise, preferably about 20 to about 200 centipoise. The weight percent fraction of PDMS in the final composition ranges from about 35 to about 80 wt/wt %, and preferably about 70 wt/wt %.

The hydrophobic continuous phase may further comprise a non-aqueous solvent. As used herein, the term "non-aqueous" means a solvent other than water. A non-aqueous solvent preserves the water-repelling property of the hydrophobic continuous phase. Suitable non-aqueous solvents include, but are not limited to, dimethylsulfoxide, dichloromethane, tetrahydrofuran, and chloroform. A short chain aliphatic, which may be used as the hydrophobic continuous phase, may also serve as a non-aqueous solvent.

In some embodiments, a secondary or ternary non-aqueous base inclusive of other aliphatic or silicone based short chain or polymeric compounds may be included in the composition at preferred weight percent fractions ranging from about 1.0 wt/wt % to about 90 wt/wt %.

Disperse Hydrophilic Phase

The composition comprises a disperse hydrophilic phase comprising at least one hydrophilic substance. As used herein, the term "disperse phase" means a solid or liquid which is suspended or dispersed within the hydrophobic continuous phase. As used herein, the term "hydrophilic" means having an affinity for water. As used herein, the term "disperse hydrophilic phase" means a phase having an affinity for water, and in which a solid or liquid is suspended or dispersed within the hydrophobic continuous phase.

In some embodiments, the disperse hydrophilic phase may confer the property of thixotropy upon the resultant composition. As used herein, the term "thixotropy" refers to a time-dependent shear-thinning property, wherein the composition is more viscous under static conditions and becomes less viscous and flows over time when subjected to an applied stress such as, for example, agitation, shaking, or shearing. Preferably, the composition has a static viscosity ranging from about 5 centipoise to about 1,000,000 centipoise, more preferably ranging from about 10 centipoise to about 500,000 centipoise, and most preferably ranging from about 10 centipoise to about 10,000 centipoise. The disperse hydrophilic phase may confer non-Newtonian behaviors to the composition, thereby easing application or transfer of the composition on the skin or a surface (for example, a dressing) or in processing. The viscosity of the composition decreases as the shear rate increases (see FIG. 1). Preferably, the apparent viscosity of the composition is decreased by at least 2-fold with applied shear rate ranging from about 10 to about 1000 1/s, and more preferably, by 10 to 100-fold with applied shear rate ranging from about 10 to about 1000 1/s. An increase in viscosity upon shear cessation results in an increase in apparent viscosity of the composition, aiding in retention of the composition once applied or positioned in a desired location. Preferably, discontinuation of shear forces results in an incremental increase in viscosity of the composition greater than about 2-fold with reducing shear rate from about 1000 to about 10 1/s, and more preferably, by 5 to 100-fold with reducing shear rate from about 10 to about 1000 1/s. The viscosity of the composition can thus be varied, affording desirable textural characteristics for various applications of the final composition.

In some embodiments, the disperse hydrophilic phase may comprise nanostructured silica. As used herein, the term "nanostructured silica" means silica having at least one dimension of 100 nanometres or less in size. As used herein, the term "silica" or "silicon dioxide" refers to an oxide of silicon with the chemical formula $SiO_2$. Preferably, the amount of nanostructured silica is greater than or equal to about 0.1 wt/wt % nanostructured silica, more preferably greater than about 3.0 wt/wt % nanostructured silica, and most preferably, a combination of nanostructured silica of greater than about 5.0 wt/wt %.

As non-limiting examples, the nanostructured silica may be in the form of fumed silica and/or nano silica. As used herein, the term "fumed silica" refers to a fine particulate or colloidal form of silicon dioxide which may be prepared by burning silicon tetrachloride in an oxygen-rich hydrogen flame to produce a smoke of silicon dioxide. Droplets of silicon dioxide are thereby fused into branched, chainlike, three-dimensional secondary particles which then agglomerate into tertiary particles with a particle size at nanoscale. Fumed silica has an extremely low bulk density and high surface area to volume ratio. Its three-dimensional structure results in viscosity-increasing, thixotropic behavior. As used herein, the term "nano silica" refers to amorphous silicon dioxide with a particle size at nanoscale, having a high surface area to volume ratio. The property of a high surface area to volume ratio shared by each of fumed silica and nano silica provides a greater potential for attracting water which may chemically react when in contact with the oxidizing agent.

The fumed silica and/or nano silica are incorporated into the composition at a total weight percent from about 1.0 wt/wt % to about 30 wt/wt %. In certain embodiments, fumed silica and nano silica are incorporated into the composition at a mass substitution ratio ranging from 1.0 to 0.1, preferably from 1.0 to 1:3, where substitution of each 1 wt/wt % fumed silica requires the addition of 3 wt/wt % nano silica. In certain embodiments where fumed silica is the sole silica component, a 2 wt/wt % to 9 wt/wt % mass fraction is preferred.

Oxidizing Agents

The composition comprises an oxidizing agent which may exhibit various properties including oxidizing effects and therapeutic activity, such as antimicrobial, anti-inflammatory, antiseptic, antifungal, antiviral, or other activity. The oxidizing agent may be locally or systemically acting, and may be administered to a subject by any suitable application including, but not limited to, topical application. The oxidizing agent is distinguishable from such components as the hydrophobic continuous phase, the dispersing hydrophilic phase, and the excipients described herein.

As used herein, the term "oxidizing agent" means a substance which has the ability to oxidize other substances or cause them to lose electrons. In some embodiments, the oxidizing agent may be susceptible to decomposition or reactivity due to factors including, but not limited to, moisture, air, heat, and light. In some embodiments, the oxidizing agent may have a reduction potential greater than 0 V vs. standard hydrogen electrode ("SHE"). In some embodiments, the oxidizing agent may have a reduction potential greater than +0.78 V versus a SHE. As used herein, the term "reduction potential" refers to a measure in volts of the tendency of a chemical species to acquire electrons and thereby be reduced. As used herein, the SHE is the reference from which all standard reduction potentials are determined, with hydrogen's standard electrode potential being 0.0 V at all temperatures for comparison with other electrode reactions.

In some embodiments, the oxidizing agent may comprise, consist of, or consist essentially of a metal or a combination of metals. As used herein, the term "metal" refers to a metal in the form of a metallic form, alloy, ion, compound, or complex. In some embodiments, the metal may comprise a transition, lanthanide, or actinide metal in an oxidized state greater than a metallic state. As used herein, the term "metallic state" as pertaining for example, to silver, means silver Ag(0) where the metal may lose electrons to form cations in a variety of oxidation states. In some embodiments, the metal may comprise silver, gold, copper, tin, titanium, zinc, iron, manganese, cobalt, platinum, nickel, cerium, or mixtures of such metals with the same or different metals, with silver being most preferred.

In some embodiments, the metal may comprise silver with a reduction potential greater than 0 V vs. SHE. In some embodiments, the metal may comprise silver with a reduction potential greater than +0.78 V versus SHE. For example, this would apply to silver in any oxidation state greater than soluble silver (I), namely silver (II) and silver (III). More preferably, the metal comprises silver with at least one element in a higher oxidation state of silver Ag(II) or Ag(III) oxidation states or a combination thereof. These oxidized species may include, but are not limited to, silver fluoride, silver bipyridine, silver carbamate, silver pyridinecarboxylic acid, a silver porphyrin, silver biguanide, a silver oxide including AgO, $Ag_2O_2$, $Ag_4O_4$, $Ag_2O_3$, $Ag_3O_4$, $Ag_7O_8X$, wherein X comprises $HCO_3^-$, $BF_4^-$, $CO_3^{2-}$, $NO_3^-$, $ClO_4^-$, $SO_4^{2-}$, or $F^-$, or a combination thereof. Most preferably, the metal comprises silver oxynitrate, $Ag_7NO_{11}$. In order for silver to exhibit its antimicrobial property, it must be in its ionized form. Contact with moisture such as water may release silver ions (Ag*) which may become incorporated by the bacteria, irreversibly damaging key enzyme systems in the cell membranes.

The weight percent concentration of silver in the composition may range from about 0.1 wt/wt % to about 50 wt/wt %, more preferably between about 3 wt/wt % to about 35 wt/wt %, and most preferably about 10 wt/wt % silver.

The metal compound may be inclusive within an inorganic framework or compound, preferably as a metal, metal oxide or metal fluoride, with or without counterions including but not limited to nitrates, carbonates, phosphates, sulfates, chlorides, fluorides, perchlorates, tellurates, periodates, peroxides, permanganates, persulfates, borates, arsenates, or combinations thereof.

Metal complexes may include, but are not limited to, tellurates, periodates, peroxides, perchlorates, permanganates, persulfates, phosphates, borates, carbonates, arsenates, or combinations thereof. Within a metal complex, the metal may form bonds with donor ligands including those in Groups VIB, VB, IIIB, and IVB including, but not limited to, dithiocarbamates, aliphatic and aromatic dithioloates, selenium ligands, sulfur ligands, ethylenediaminetetraacetic acids, imine ligands, oxime ligands, dimethylglyoxime, macrocylic amines, porphyrins, tetraazacyclohexadiene, pyridine, pyrazine, bipyridyl, phenanthrolines, dimethylphosphines, dimethylarsines, dibutylthioureas, ethylenediimines, polypeptides, guanides, biguanides, polyguanides, phosphines, arsines, or combinations thereof.

In some embodiments, the oxidizing agent may comprise, consist of, or consist essentially of a metalloid. As used herein, the term "metalloid" refers to an element whose properties are intermediate between those of metals and solid non-metals. Suitable metalloids include, but are not limited to, boron, borates, and borane, which exhibit antiseptic, antifungal, and antiviral properties against various protozoans responsible for tropical diseases.

In some embodiments, the oxidizing agent may comprise, consist of, or consist essentially of a polyatomic non-metal. As used herein, the term "polyatomic non-metal" refers to an element which lacks metallic attributes and contains more than one atom. Suitable polyatomic non-metals include, but are not limited to, tellurates, periodates, peroxides, perchlorates, permanganates, persulfates, selenium and graphene or higher order carbon nanostructures. Selenium increases immunity, defends against free radical damage and inflammation, and is present in several proteins that play a critical role in maintaining cellular redox homeostasis. Graphene or higher order carbon nanostructures are strongly hydrophobic, where oxidized graphene acts as a peroxidase-like mimetic.

Excipients

As used herein, the term "excipient" means any ingredient which is added optionally to a composition of the present invention, other than the hydrophobic continuous phase, disperse hydrophilic phase, and oxidizing agent which are each described separately above. Suitable excipients include, but are not limited to, Pickering agents, surface-active agents, hydrogeling agents, hygroscopic agents, opacifying agents, masking agents, and combinations thereof.

As used herein, the term "Pickering agent" refers to solid particles which accumulate at the interface between two immiscible liquids (typically denoted as an oil and water phase) and stabilize droplets against coalescence. Preferably, the particle has a size smaller than the droplets of the disperse hydrophilic phase and does not have a tendency to form an agglomerate. More preferably, the particle size is less than 35 mesh or about 500 microns, and most preferably, less than 200 mesh or about 74 microns. Preferably, the amount of the Pickering agent is greater than or equal to about 0.1 wt %, more preferably greater than about 5.0 wt %, and most preferably, greater than about 15.0 wt %.

Selection of the Pickering agent is such that the solid particle is wettable by both the hydrophobic continuous phase and aqueous phase at an aqueous or moist interface. Selection of the Pickering agent is such that the mesh size of the solid particle is amenable to stabilization of a water in oil interface and texturally smooth within the composition. More particularly, the Pickering agent may also confer optical characteristics of the composition including opacity, tone, and hue or to the textural or physical properties such as absorbency, viscosity, and humectant nature of the composition.

Suitable Pickering agents include, but are not limited to, inorganic and organic microparticles and nanoparticles. As used herein, the term "microparticle" means a particle between 1 and 1000 micrometres in size. As used herein, the term "nanoparticle" means a particle having at least one dimension of 100 nanometres or less in size. Non-limiting examples of inorganic microparticles and nanoparticles include minerals and clays. Metals, metal oxides, and metal sulfates, which may be used as oxidizing agents, may also serve as Pickering agents. Silica, which may be used as the disperse hydrophilic phase, may also serve as a Pickering agent. Non-limiting examples of organic microparticles and nanoparticles include chitosan, cyclodextrin, starch, alginate, microcrystalline cellulose, nanocrystalline cellulose, and combinations thereof.

As used herein, the term "surface-active agent" refers to a surfactant or substance which lowers the surface tension of the medium in which it is dissolved, the interfacial tension with other phases, and is positively adsorbed at the liquid-vapour interface and other interfaces. Surface-active agents may be incorporated into the composition, particularly within the hydrophobic continuous phase. Suitable surface-active agents include, but are not limited to, alkyl sulfonates, alkyl quaternary ammoniums, imides, imines, and polymeric structures such as block co-polymers of alkanes, alkylsiloxanes, ethylene glycols, vinyl pyrrolidones, vinyl alcohols, acrylic acids, or phosphates, and combinations thereof. More preferably, the surface-active agent is selected from an alkyl sulfonate, alkyl quaternary ammonium, and/or polymeric block co-polymer of alkylsiloxane and ethylene glycol, or a combination thereof. In some embodiments, the surface-active agent may be polyethylene glycol/polypropylene glycol dimethicone (PPD) or cetyltrimethylammonium. Preferably, the amount of the surface-active agent is greater than or equal to about 0.1 wt/wt %, and more preferably, ranges from about 0.5 wt/wt % to about 10.0 wt/wt %. The weight percent concentration of the surface-active agent ranges from about 0.1 to about 10 wt/wt %, more preferably from about 0.5 to about 1 wt/wt %. At concentrations greater than about 0.5 wt/wt %, PPD alteration of the rheological properties may be achieved, diminishing the thixotropic properties of the composition.

As used herein, the term "hydrogeling agent" refers to a polymer having an ability to swell through the absorption or retention of water and is composed of a polymer material which, when brought into contact with water or other aqueous solvents, can undergo swelling to some extent through the absorption of such water/solvent. The hydrogeling agent can be anhydrous (i.e., contain no water). Preferably, the constitution of water in the anhydrous hydrogeling agent is less than about 8.0 wt/wt %, and more preferably, less than about 2.0 wt/wt %. Suitable hydrogeling agents include, but are not limited to, polymeric carbohydrates, saccharides, acids, alcohols, pyrrolidones, bentonite, carbopols, carrageenan, xanthan gum, and combinations thereof. In some embodiments, the amount of hydrogeling agent may range between about 0.1 and about 10.0 wt/wt %, and more preferably about 0.5 wt/wt %. Alginate, alginic acid, starch, and cellulose (for example, carboxymethylcellulose and microcrystalline cellulose), which may be used as Pickering agents, may also serve as hydrogeling agents.

As used herein, the term "hygroscopic agent" refers to a substance which attracts and readily absorbs water molecules from the surrounding environment. Non-limiting examples of hygroscopic agents include vegetal fibers (e.g., cellulose), sugar, glycerol, ethanol, methanol, and salts including sodium carbonate, calcium chloride, magnesium sulfate, and bases such as sodium hydroxide). Suitable hygroscopic agents include but are not limited to: sulfate salts including magnesium, sodium and potassium, methylated cellulose, polyacrylates such as polyacrylic acid and salts thereof, and silica gel.

As used herein, the term "opacifying agent" refers to an additive which may be added to the composition to alter its tone or shade. Suitable opacifying agents include, but are not limited to, titanium dioxide, zinc sulfate, zirconium oxide, zinc oxide, dolomite, barium sulfate, calcium carbonate, talc, and mica. Calcined clay and silica, which may be used as Pickering agents, may also serve as opacifying agents. In some embodiments, the opacifying agent may be titanium dioxide which is preferably oil-dispersible. The weight percent concentration of titanium dioxide ranges between about 1.0 wt/wt % to about 10 wt/wt %, and more preferably between about 6.0 wt/wt % to about 8.0 wt/wt %.

As used herein, the term "masking agent" refers to an additive which may be added to the composition to alter the perceived color. Suitable masking agents include, but are not limited to, carbon black, pyrophyllite, alumina, aluminum, bismuth oxychloride, talc, and mica. Talc and mica, which may be used as opacifying agents, may also serve as masking agents. Preferably the masking agent is aluminum powder with a mesh size ranging from 200 to 300 mesh size, and most preferably, 300 mesh size. The weight percent concentration of the masking agent ranges from about 1.0 wt/wt % to about 10 wt/wt %, and more preferably ranges from about 7 wt/wt % to about 9 wt/wt %.

Preparation of the Composition

The composition may be prepared by selecting particular components and proportions based on the desired characteristics of the composition. The composition may be prepared by combining the hydrophobic continuous phase, the oxidizing agent, and optionally, one or more excipients, with the disperse hydrophilic phase. In some embodiments, the composition may be prepared by mixing the hydrophobic continuous phase, the oxidizing agent, and optionally, one or more excipients, to form a mixture, and then adding the disperse hydrophilic phase in portions to the mixture to form the composition. In some embodiments, the disperse hydrophilic phase may be added in at least two portions to ensure thorough mixing.

The composition may be prepared at low temperatures without requiring a thermal or melt phase, or heat/cool cycles, and preferably at ambient temperatures ranging from 0° C. to 60° C., more preferably below room temperature or less than 25° C., and most preferably between 10° C. to 25° C.

In preparing the mixture, the composition may be formed by mixing the components in any order. In some embodiments, the hydrophobic continuous phase and optionally, one or more excipients, may be first mixed together before adding the oxidizing agent in order to minimize the shear heat of mixing. Preferably, addition of the oxidizing agent is conducted below 60° C., more preferably below 25° C., and most preferably between 10° C. and 25° C. Dispersion of the oxidizing agent in the mixture is achieved through high shear mixing. In some embodiments, high shear mixing may be conducted at 2000 rpm for 5 minutes at room temperature. The disperse hydrophilic phase is the final component to be added, and results in a viscosity change of the final composition. In some embodiments, the disperse hydrophilic phase is added in portions to the mixture to form the composition and may be added in at least two portions to ensure thorough mixing. No further excipients are included as such addition would result in inadequate dispersion and a coarse undesirable texture. In some embodiments, the components are thus mixed in the following sequence to form the composition: hydrophobic continuous phase; optionally, one or more excipients; oxidizing agent; and disperse hydrophilic phase.

In some embodiments, the one or more excipients may comprise one or more of an opacifying agent, a masking agent, a hydrogeling agent, and a surface-active agent which are mixed in sequence with the hydrophobic continuous phase.

In some embodiments, the composition may comprise siloxane, titanium dioxide, aluminum powder, carboxymethyl cellulose, PEG/PPG dimethicone, and silver oxynitrate. In some embodiments, each component may be mixed at 2000 rpm for about 5 minutes.

In some embodiments, a secondary or ternary non-aqueous base may be included in the composition at preferred weight percent fractions ranging from about 1.0 wt/wt % to about 90 wt/wt %. Preferably, the secondary or ternary non-aqueous base is dispersed into the composition by mixing (for example, at 2000 rpm for 5 minutes) at or greater than room temperature to facilitate mixing, more preferably by mixing above the melt transition temperature of the wax and permitting a cooling step to occur while mixing to return the temperature of the dispersed media to below the melt transition temperature, more preferably to below 25° C. prior to the addition of other composition components.

In certain embodiments, the composition may be applied as a coating to a secondary surface, interface, or substrate (for example, a medical device, dressing, a semi-occlusive or moisture/vapor permeable barrier) by means of air-knife blowing, rotogravure printing, dipping, rolling, screening, slot-die coating, spraying, spinning, printing, or a combination thereof. To facilitate coating of the composition to the secondary surface, interface, or substrate, a solvent may be added during the coating process. Preferably, the solvent exhibits a boiling point below 100° C., more preferably below 60° C., and most preferably below 40° C. Suitable solvents include, but are not limited to, dichloromethane, chloroform, tetrahydrofuran, acetone, and cyclomethicones. Alternatively, to increase flowability, polymerization precursors exhibiting a lower viscosity than that of the hydrophobic continuous phase may be included in the coating. Polymeric precursors include, but are not limited to, halosilanes and alkoxysilanes.

Exemplary Compositions and their Uses

The compositions of the present invention may be used in various applications including, but not limited to, medical, dental, pharmaceutical, cosmeceutical, personal care, veterinary, agricultural, materials engineering, and over-the-counter fields. Exemplary compositions of this invention are biocompatible and intended for medical applications. As used herein, the term "biocompatible" means generating no significant undesirable host response for the intended utility. Most preferably, biocompatible compositions are non-toxic for the intended utility. Thus, for human utility, biocompatible is most preferably non-toxic to humans or human tissues.

Certain embodiments of the invention thus relate to methods and uses of the compositions to deliver oxidizing agents, or both to a cell. In some embodiments, the invention may comprise a method of treating, preventing, or ameliorating a disease or disorder in a subject, comprising administering the composition comprising the oxidizing agent to the subject. As used herein, the terms "treating," "preventing." and "ameliorating" refer to interventions performed with the intention of alleviating the symptoms associated with, preventing the development of, or altering the pathology of a disease, disorder or condition. Thus, in various embodiments, the terms may include the prevention (prophylaxis), moderation, reduction, or curing of a disease, disorder or condition at various stages. In various embodiments, therefore, those in need of therapy/treatment may include those already having the disease, disorder or condition and/or those prone to, or at risk of developing, the disease, disorder or condition and/or those in whom the disease, disorder or condition is to be prevented. As used herein, the term "disease" or "disorder" refers to any condition characterized by infection, inflammation, or a combination thereof. As used herein, the term "subject" means a human or other vertebrate. The composition comprising an oxidizing agent is useful for treating, preventing, or ameliorating a disease or disorder upon administration. The composition provides either subjective relief of symptoms or an objectively identifiable improvement as noted by the clinician or other qualified observer.

In some embodiments, administration may be topical, with the composition comprising the oxidizing agent being applied to the locally affected area of the skin. In some embodiments, the invention may comprise use of the composition comprising the oxidizing agent to treat, prevent, or ameliorate a disease or disorder in a subject.

A single application of the composition of the present invention may be sufficient, or the composition may be applied repeatedly over a period of time, such as several times a day for a period of days or weeks. The amount of the oxidizing agent will vary with the condition being treated, the stage of advancement of the condition, the age and type of host, and the type and concentration of the composition being applied. Appropriate amounts in any given instance will be readily apparent to those skilled in the art or capable of determination by testing compositions containing the oxidizing agent by in vitro or in vivo testing.

Exemplary compositions of this invention for medical applications include compositions comprising oxidizing agents which may exhibit antimicrobial and/or anti-inflammatory activity. The oxidizing agent may be locally or systemically acting. The oxidizing agent may be administered to a subject by application of the composition (for example, topically by applying the composition or coated dressing directly to abraded skin, lacerations, wounds, burns, surgical incisions, etc.).

Figure 8:
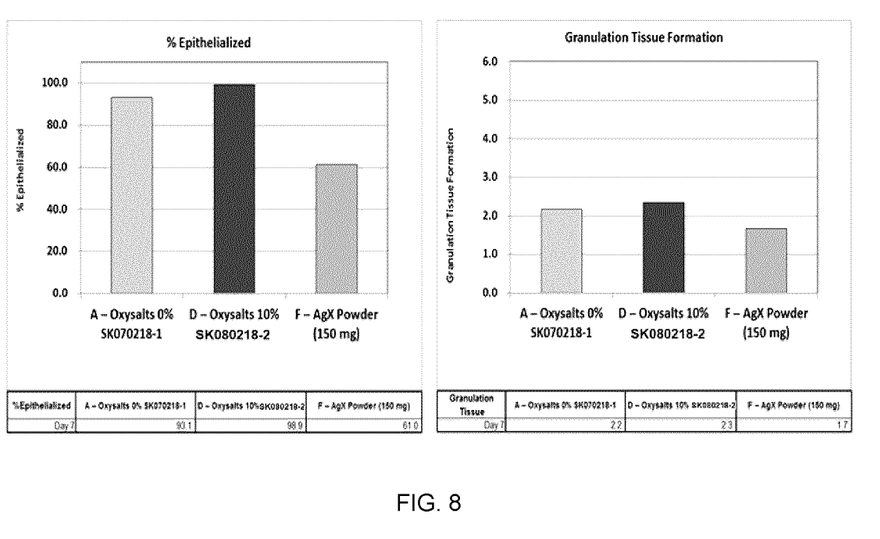
FIG. 8 are graphs showing histological data for the application of various semi-solid compositions and positive controls after 7 days on a *P. aeruginosa* PA 2732 infected porcine burn model (left—percent wound epithelization; right—granulation tissue formation).
Figure 9:
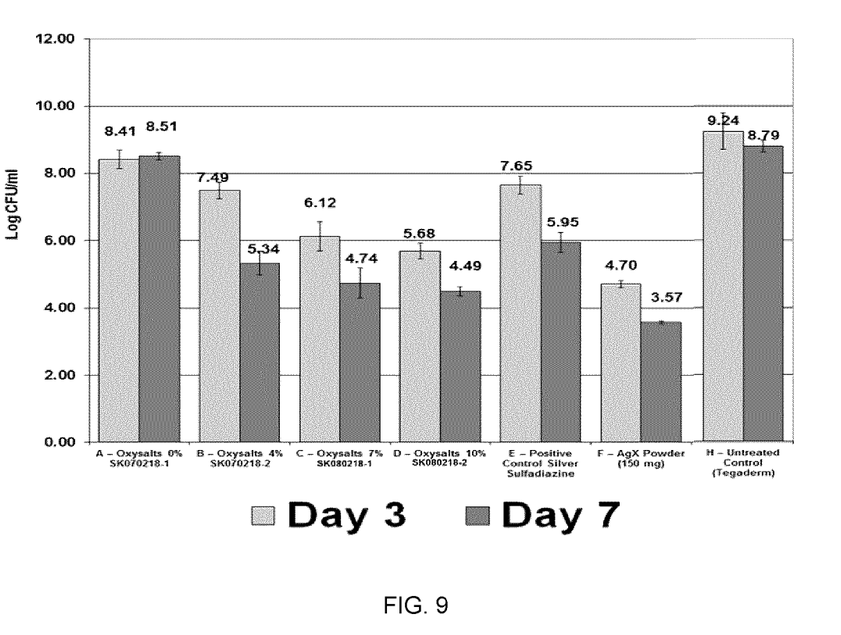
FIG. 9 is a graph showing bacterial counts after treatment application of various semi-solid compositions and positive/negative controls after 3 and 7 days on a *P. aeruginosa* PA 2732 infected porcine burn model.

In some embodiments, the disease or disorder may be characterized by infection caused by microbes such as, for example, bacteria, viruses, fungi, and protozoa. Bacteria include, but are not limited to, *Staphylococcus aureus* and *Pseudomonas aeruginosa*. In an exemplary embodiment, the disorder may be a skin infection (for example, pimples, impetigo, boils, cellulitis, folliculitis, carbuncles, scalded skin syndrome, and abscesses) caused by *Staphylococcus aureus* which may be treated using the composition comprising silver oxynitrate as the oxidizing agent (see Examples 1-3; FIGS. 2-4 and 10). In an exemplary embodiment, the disorder may be a burn (for example, a second-degree wound) requiring treatment of infection by a bacterium such as, for example, *Pseudomonas aeruginosa*, using the composition comprising silver oxynitrate as the oxidizing agent (see Example 1; FIGS. 8 and 9).

Figure 5:
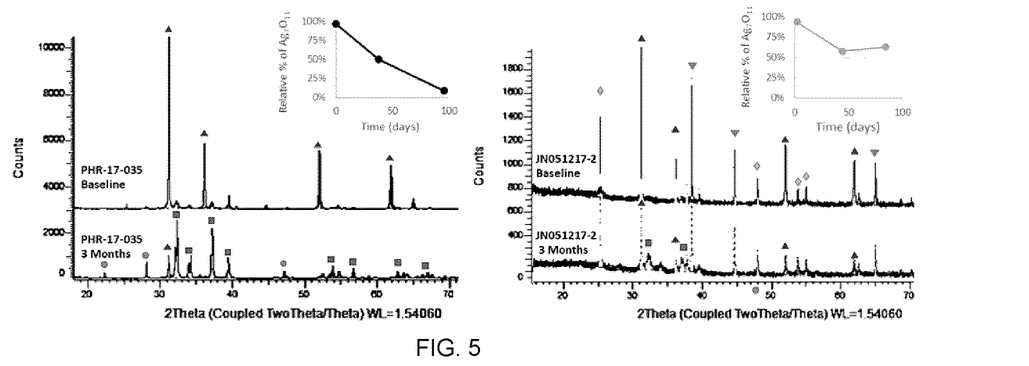
FIG. 5 shows the time-lapsed X-ray powder diffraction pattern of silver oxynitrate in an unformulated, powder format (PHR-17-035) on the left and of semi-solid composition (JN051217-1, 7 wt/wt % Ag) on the right; X-ray patterns taken at baseline (time zero) and 3 months. Patterns of each solid-state species are denoted as silver oxysalts (triangle), AgO (square), $Ag_2SO_4$ (circle), $TiO_2$ (diamond), and aluminum (inverted triangle). Within each figure is an inlay of the percent relative main peak height of silver oxynitrate versus the main solid-state degradation products, including AgO, $Ag_2O$ and $Ag_2SO_4$.

Further, the composition may confer enhanced stability to the oxidizing agent, thereby preventing or minimizing degradation. As used herein, the term "stability" means the tendency of the composition to resist degradation when exposed to an internal reaction, natural condition, or environment. As used herein, the term "degradation" means the incapacity or incapability of a composition to remain within a particular chemical, microbiological, therapeutical, physical specification, or combination thereof. Physical signs of degradation may include, but are not limited to, separation, flocculation, precipitation, and the like. This stability may be enhanced compared to traditional compositions or materials independent of the composition as evaluated by the fraction of the original materials or primary decomposition products over time. In an exemplary embodiment, the oxidizing agent (i.e., silver oxynitrate) may exhibit enhanced immediate and long-term stability within the composition (see Example 1; FIG. 5). Such observed stability indicates that the composition may confer a long shelf-life to the oxidizing agent.

Embodiments of the present invention are described in the following Examples, which are set forth to aid in the understanding of the invention and should not be construed to limit in any way the scope of the invention as defined in the claims which follow thereafter.

Example 1

Amounts of specific compounds were weighed out as indicated in Table 1. Siloxane (PDMS) was weighed out into a 500-ml polypropylene beaker at 25° C. Titanium dioxide ($TiO_2$), aluminum powder, carboxymethyl cellulose (CMC), PEG/PPG 18/18 dimethicone (PPD), and silver oxynitrate ($Ag_7NO_{11}$) were weighed out into individual polystyrene weight boats.

TABLE 1

Masses of excipients, metal compound, and total mass of the preparation of the higher oxidation state metal compositions.

| Sample ID | PDMS | $SiO_2$ | $TiO_2$ | PPD | Aluminum | CMC | $Ag_7NO_{11}$ | Total (g) |
|---|---|---|---|---|---|---|---|---|
| JN161117-2 | 124.1 | 7.30 | 17.60 | 0.00 | 22.50 | 1.26 | 78.240 | 251.00 |
| JN161117-4 | 119.7 | 8.90 | 17.60 | 2.500 | 22.50 | 1.25 | 78.256 | 250.71 |
| JN210917-1 | 158.1 | 10.30 | 14.60 | 0.00 | 18.50 | 1.023 | 0.00 | 202.52 |
| JN020817-2 | 189.2 | 12.61 | 17.50 | 0.00 | 22.50 | 1.24 | 9.406 | 252.46 |
| JN020817-3 | 179.9 | 12.52 | 17.50 | 0.00 | 22.50 | 1.25 | 21.911 | 255.58 |
| JN151117-1 | 179 | 12.90 | 17.70 | 17.60 | 22.60 | 1.26 | 0.00 | 251.06 |
| JN151117-3 | 112 | 9.00 | 17.60 | 10.10 | 22.50 | 1.27 | 78.222 | 250.69 |
| JN151117-4 | 104.7 | 8.70 | 17.60 | 17.60 | 22.60 | 1.26 | 78.233 | 250.69 |
| JN051217-1 | 137.7 | 10.30 | 14.10 | 2.600 | 18.00 | 1 | 17.531 | 201.23 |
| JN051217-2 | 139.6 | 10.40 | 14.10 | 0 | 18.20 | 1.01 | 17.536 | 201.01 |
| JN040118-2 | 138.5 | 10.10 | 14.00 | 1.00 | 18.00 | 1.00 | 17.527 | 200.13 |
| SK070218-1 | 71 | 11.3 | 7 | 0 | 9 | 0.5 | 0 | 98.8 |
| SK070218-2 | 66 | 11.3 | 7 | 0 | 9 | 0.5 | 4 | 97.8 |
| SK080218-1 | 62.2 | 11.3 | 7 | 0 | 9 | 0.5 | 7 | 97 |
| SK080218-2 | 58.5 | 11.3 | 7 | 0 | 9 | 0.5 | 10 | 96.3 |

Using a high shear Silverson™ L5M-A Laboratory mixer, a beaker containing PDMS was placed on the base assembly, and the mixer frame was lowered into the liquid. The mixer was turned on and the timer was set to 30 minutes. The speed was gradually increased to 2,000 RPM until a full vortex was created in the liquid. Each compound was slowly added in small portions at a time to ensure thorough mixing of each compound in turn within the liquid for a specified time. After 1 minute, $TiO_2$ was added to the beaker containing the PDMS. After 5 minutes, the aluminum powder was added to the beaker. After 5 minutes, CMC was added to the beaker. After 5 minutes, PPD was added to the beaker. After 4 minutes, $Ag_7NO_{11}$ was added. The composition mixture was then left to mix at 2,000 RPM for the remaining time. Upon completion, the mixer was turned off and the mixer frame was removed from the beaker.

The beaker containing PDMS, $TiO_2$, aluminum powder, CMC, PPD and $Ag_7NO_{11}$ was placed on the top loading balance and half of the amount of fumed silica was added. The beaker was then placed back on the base assembly. The mixer frame was lowered into the beaker. The mixer was turned on and the timer was set to 5 minutes. The speed was gradually increased to 2,000 RPM. The beaker was manually rotated to assist the mixing of fumed silica into the composition. Upon completion, the mixer frame was removed from the beaker. The beaker was placed on the top loading balance and the remaining quantity of fumed silica was added. The beaker now containing PDMS, $TiO_2$, aluminum powder, CMC, PPD, $Ag_7NO_{11}$ and fumed silica was placed back on the base assembly, and the mixer frame was lowered into the liquid. The mixer was turned on and the timer was set to 5 minutes. The speed was gradually increased to 1,800 RPM. The beaker was manually rotated to assist the mixing of fumed silica into the composition. Upon completion, the mixer was turned off and the mixer frame was removed from the beaker. The composition was then transferred to the desired packaging system.

Figure 1:
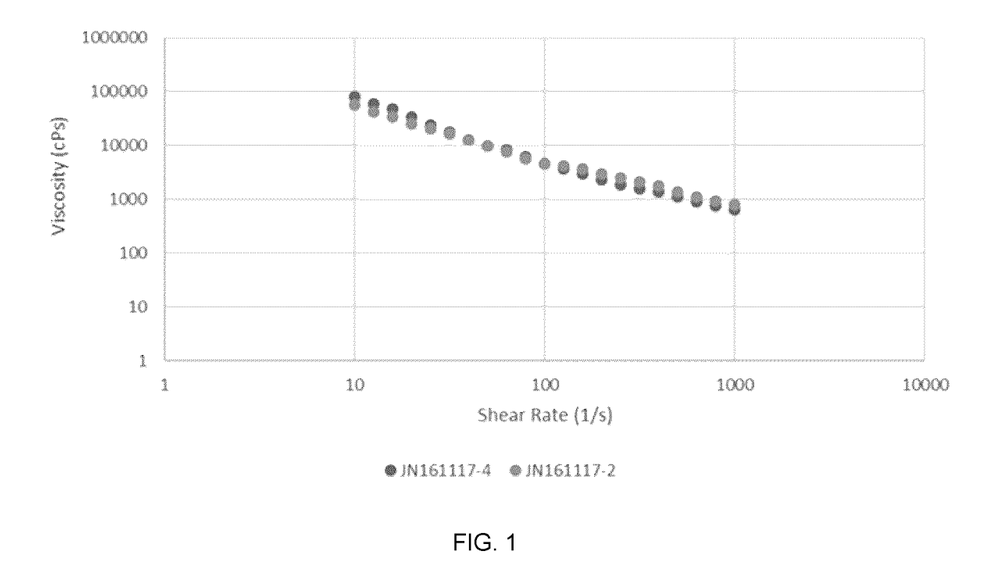
FIG. 1 is a graph showing the shear thinning properties of semi-solid compositions JN161117-4 and JN161117-2.

Shear thinning properties of therapeutic compositions (JN161117-4 (25 wt/wt % silver, 1 wt/wt % PPD) and JN161117-2 (25 wt/wt % silver, 0 wt/wt % PPD) were performed on a rheometer (AR 2000, TR Instruments) at 25° C. (Rheology Laboratory, Department of Mechanical & Industrial Engineering, University of Toronto). Briefly, approximately 1 g of the composition was applied to the rheometer cone (20 mm 4°) with the Peltier plate set to 25±0.1° C. An applied shear rate starting at 10 1/s and increasing to 1000 1/s with a rate of shear increase of 125 pa/s was applied to the composition. Apparent viscosity was reported at 20 linear sampling points over the sweep. As shown in FIG. 1, the viscosities of the compositions decreased as the shear rate increased.

The antimicrobial activities of the compositions were evaluated by exposing the composition to *Staphylococcus aureus* biofilms. Briefly, *S. aureus* biofilms were grown on sterile gauze at 37° C. for 72 hours (gauze was re-inoculated with *S. aureus* at 24 h and 48 h). After incubation, the gauze was rinsed with sterile water and placed onto Mueller Hinton agar (MHA) plates. The ointment was spread onto a piece of Parafilm™ and then inverted and placed on top of the gauze. A 250 mL beaker filled with 150 mL water was placed on top of the Parafilm/composition/gauze combination to apply pressure for the composition onto the biofilm. The plates were incubated for 6 hr at 37° C. The composition/Parafilm was removed from the biofilm and the biofilm/gauze was neutralized in 10 mL of sodium thioglycolate. The bacteria were agitated to remove them from the gauze and the resulting bacterial suspensions were diluted and spread onto MHA plates which were incubated for 18-24 h at 37° C. and the resulting viable bacterial colonies were enumerated. The log-reduction of *S. aureus* was calculated relative to the reduction achieved in the "no treatment" negative control samples.

Figure 2:
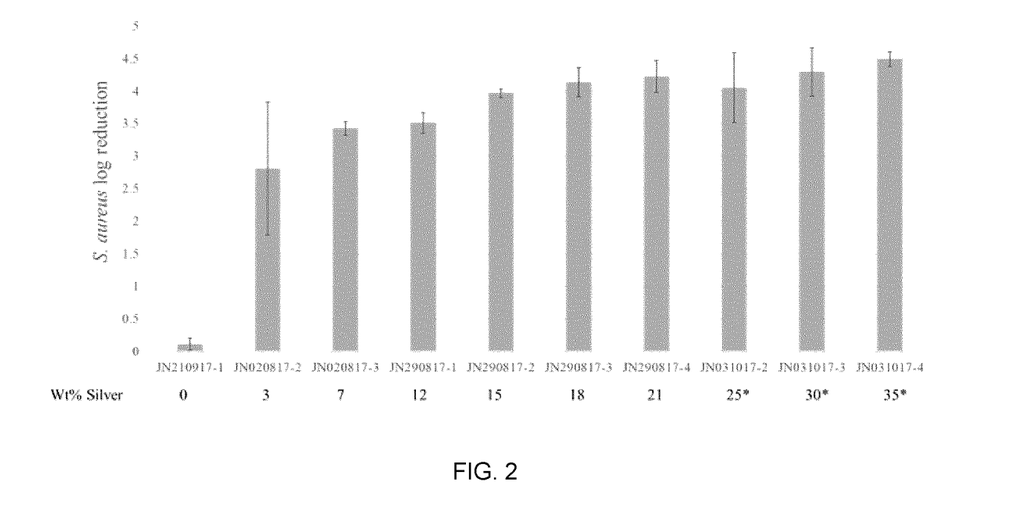
FIG. 2 is a graph showing results of a *S. aureus* antibiofilm assay using compositions containing increasing weight/weight percent concentrations of silver ($Ag_7NO_{11}$), with results representing the average of triplicate data.

As shown in FIG. 2, an increase in anti-biofilm activity was achieved through an increase in the concentration of oxidizing agent (i.e., silver oxynitrate) in the composition (JN210917-1, 0 wt/wt % Ag; JN020817-2, 3 wt/wt % Ag, JN020817-3, 7 wt/wt % Ag).

Figure 3:
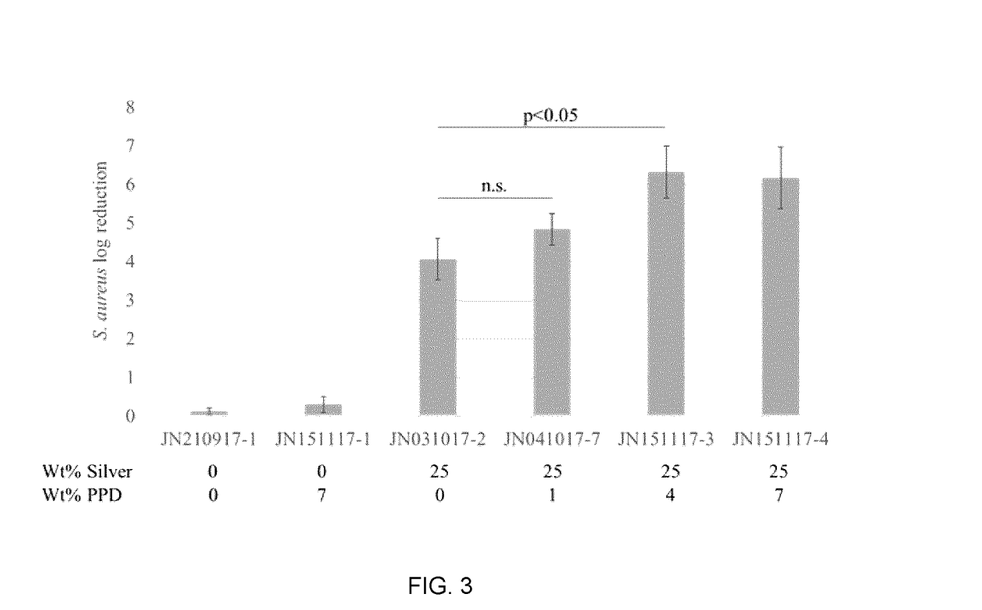
FIG. 3 is a graph showing results of a *S. aureus* antibiofilm assay using compositions containing 0 or 25 wt/wt % Ag as $Ag_7NO_{11}$ and/or 0, 1, 4, or 7 wt/wt % PEG/PPG 18/18 dimethicone, with results representing the average of technical triplicate data.

As shown in FIG. 3, incremental anti-biofilm activity was achieved through increasing PEG/PPG 18/18 dimethicone (PPD) composition within the composition, independent of PPD in isolation (JN210917-1, 0 wt/wt % Ag, 0 wt/wt % PPD; JN151117-1, 0 wt/wt % Ag, 7 wt/wt % PPD; JN151117-3, 25 wt/wt % Ag, 4 wt/wt % PPD; JN151117-4, 25 wt/wt % Ag, 7 wt/wt % PPD).

Figure 4:
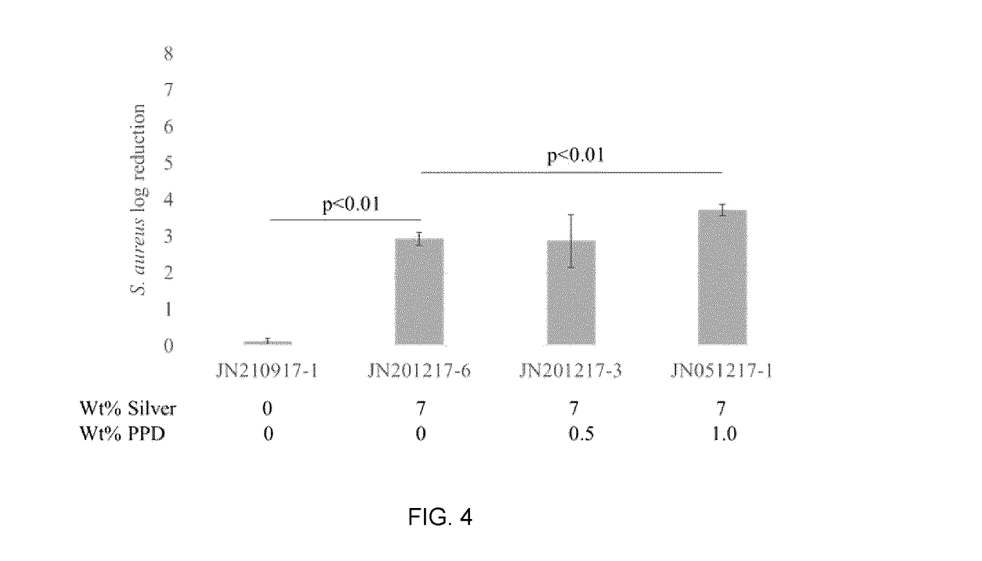
FIG. 4 is a graph showing results of a *S. aureus* antibiofilm assay comparing efficacy of samples containing 0 or 7 wt/wt % Ag as $Ag_7NO_{11}$ and/or 0, 0.5, and 1 wt/wt % PPD PEG/PPG 18/18 dimethicone, with results representing the average of triplicate data.

As shown in FIG. 4, a significant increase in the anti-biofilm activity was obtained upon the inclusion of the oxidizing agent (i.e., silver oxynitrate) within the composition, with a further significant improvement upon the addition of PPD (JN210917-1, 0 wt/wt % Ag, 0 wt/wt % PPD; JN051217-1, 7 wt/wt % Ag, 1 wt/wt % PPD).

Using a Bruker™ X-ray powder diffractometer, the immediate and long-term stability of oxidizing agents (i.e, silver oxynitrate) within the composition were determined. As seen in FIG. 5, degradation of the solid-state oxidizing agent was evaluated within the composition (JN051217-1, 7 wt/wt % Ag) versus silver oxynitrate in an unformulated, powder format (PHR-17-035). The X-ray diffraction patterns were obtained. Using the percent relative main peak height of silver oxynitrate versus the main solid-state degradation products, including AgO, $Ag_2O$ and $Ag_2SO_4$, a degradation profile was tracked, demonstrating the enhanced stability of silver oxynitrate within the semi-solid composition.

Figure 6:
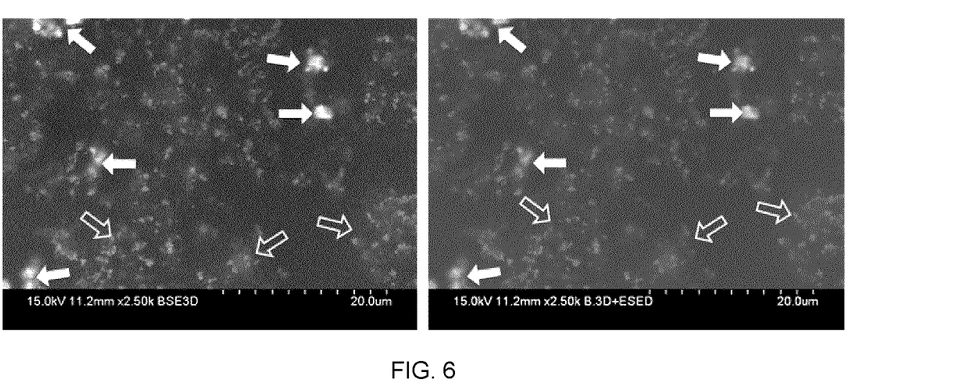
FIG. 6 shows scanning electron micrographs taken at 15.0 kV, scale bar equivalent to 20 micrometer, of composition JN040118-2 (left—back scattering electron image in 3D; right—environmental secondary electron detector images; solid white arrows indicate position of silver oxynitrate; outlined white arrows indicate positions of titanium dioxide).
Figure 7:
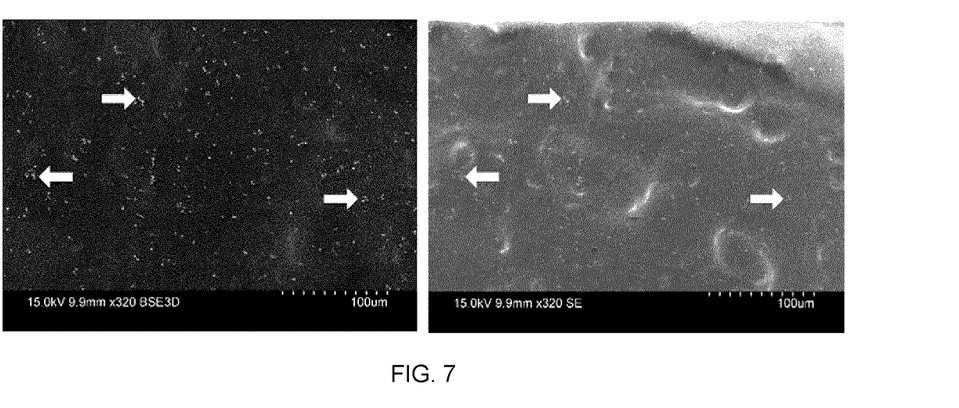
FIG. 7 shows scanning electron micrographs taken at 15.0 KV, scale bar equivalent to 100 micrometer, of carbon-coated composition JN040118-2 (left—back scattering electron image in 3D; right—secondary electron emission images; solid white arrows indicate position of silver oxynitrate).

Scanning electron microscopy was performed using a Hitachi™ S-3400N 0.3-30 KV variable pressure SEM (Microscopy Imaging Laboratories, University of Toronto). Briefly, approximately 0.01 g of the composition (JN040118-2, 7 wt/wt % Ag) was applied in a thin layer to a carbon coated copper grid of 3 mm diameter. The composition was then imaged with a coating of carbon or without a coating at 15.0 kV using back scattering electron in 3D, secondary electron emission, or environmental secondary electron detector imaging. As shown in FIGS. 6 and 7, the solid white arrows indicate the positions of silver oxynitrate, while the outlined white arrows indicate positions of titanium dioxide.

Using an in vivo infected porcine burn model, second degree wounds were generated on porcine skin of 8.5 mm diameter and 0.8 mm deep, inoculated with 25 µL of $10^6$ CFU/mL *Pseudomonas aeruginosa* (ATCC 2732), sealed with a polyurethane film, and left undisturbed for 24 h to permit biofilm formation. Following baseline bacterial counts, a series of treatments were applied in triplicate to each wound bed where microbial counts were completed on days 3 and 7 and histology was performed on day 7. Silver sulfadiazine and silver oxynitrate in powder form were utilized as the positive controls and an untreated wound was isolated as the negative control. Histological assessment included percent of wound epithelialized (%) or measurement of the length of the wound surface that has been covered with epithelium and granulation tissue formation, or the approximate amount of new granulation tissue formation (dermis) graded as follows: 0=0, 0.5=1-10%, 1=11-30%, 2=31-50%, 3=51-70%, 4=71-90%, 5=91-100%.

Histological data for the application of compositions SK070218-1 and SK080218-2 and positive controls (silver oxynitrate unformulated powder, PHR-17-035) after 7 days on a *P. aeruginosa* PA 2732 infected porcine burn model (left—percent wound epithelization; right—granulation tissue formation) were determined as shown in FIG. 8. The percentage of the wound area covered by at least one or more layers of keratinocytes denoted the newly formed epidermis, serving as a valuable measure for the rate of keratinocyte migration and speed of wound healing. On the seventh day of treatment, both semi-solid compositions exhibited a higher percent of re-epithelialization over unformulated silver oxynitrate powder alone. A similar trend was observed for the composition of granulation tissue, inclusive of angiogenesis, fibroblasts and collagen matrices, demonstrating the therapeutic benefit of the semi-solid compositions.

FIG. 9 shows the bacterial counts after application of the compositions SK070218-1, SK070218-2, SK080218-1, SK080218-2, positive controls (silver sulfadiazine, SSD), and negative controls (Tegaderm untreated) after three and seven days on a *P. aeruginosa* PA 2732 infected porcine burn model. After both three and seven days of treatment, semi-solid compositions containing oxidizing agent (i.e., silver oxynitrate) were observed to have improved efficacy over both the semi-solid composition control containing no silver oxynitrate and the positive control (SSD). Seven days of treatment with SK080218-2 (10 wt/wt % Ag) resulted in bacterial biofilm reductions of 99.99%, demonstrating an improved biocidal activity over the positive control of SSD.

Example 2

Amounts of compounds were weighted out as indicated in Table 2:

TABLE 2

Masses of excipients in grams (g), oxidizing agent, and total mass of the preparation of the semi-solid compositions.

| | | | Composition Base | | |
|---|---|---|---|---|---|
| Sample ID | $Ag_7NO_{11}$ | $SiO_2$ | (g) | Composition | Total (g) |
| CS180316-4 | 0.1501 | 0.000 | 4.0038 | Petrolatum Jelly | 4.1539 |
| CS040816-6 | 0.3744 | 0.0256 | 9.6000 | Diaper cream: 15 wt % ZnO, 80.3 wt % petrolatum, lanolin, paraffin, ceral alba | 10.0000 |

The composition base was weighed out into a ceramic mortar at 25° C. $Ag_7NO_{11}$ powder and $SiO_2$ were added to the mortar containing PDMS and manually mixed for about 5 min to yield a homogenous dark grey-colored mixture.

Figure 10:
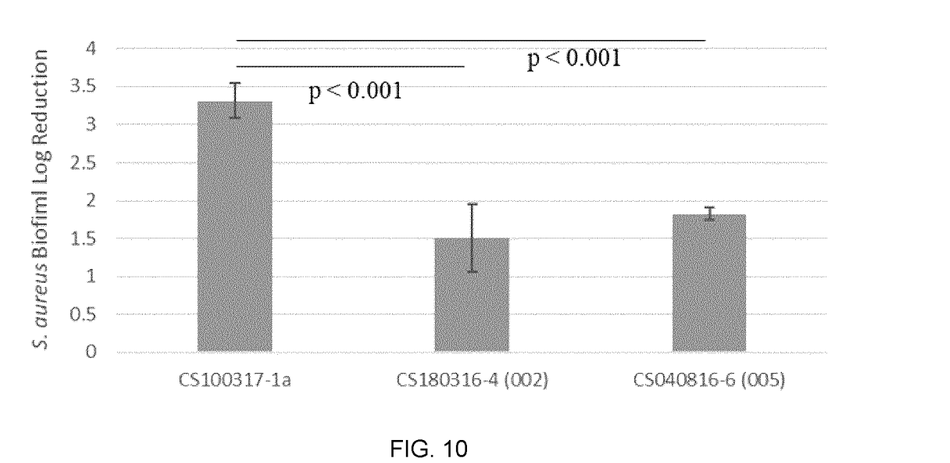
FIG. 10 is a graph showing results of a *S. aureus* antibiofilm assay comparing efficacy of samples containing 3.0 wt/wt % Ag as $Ag_7NO_{11}$ in a petrolatum base (CS180316-4, 002), in a petrolatum zinc oxide base (CS040816-6, 005) and as prepared in methods described herein (CS100317-1a), with results representing the average of triplicate data.

The antimicrobial activities of the compositions were evaluated by exposing the composition to *Staphylococcus aureus* biofilms using same method described in Example 1. As shown in FIG. 10, significantly lower anti-biofilm activity was observed for simple ointment (CS180316-4, 002) and paste (CS040816-6, 005) compositions in comparison to the semi-solid compositions described below (CS100317-1a), demonstrating the superior performance of oxidizing agents within the semi-solid compositions described herein.

Example 3

Amounts of specific compounds were weighed out as indicated in Table 3:

TABLE 3

Masses of excipients in grams (g), oxidizing agent, and total mass of the preparation of the semi-solid compositions.

| Sample ID | PDMS | $SiO_2$ | $TiO_2$ | PPD | Aluminum | CMC | $Ag_7NO_{11}$ | Total (g) |
|---|---|---|---|---|---|---|---|---|
| JN290817-1 | 20.13 | 1.47 | 2.52 | 0.00 | 2.80 | 0.15 | 4.517 | 31.59 |
| JN290817-2 | 19.19 | 1.53 | 2.16 | 0.00 | 2.72 | 0.152 | 5.639 | 31.39 |
| JN290817-3 | 18.17 | 1.40 | 2.19 | 0.00 | 2.84 | 0.153 | 6.758 | 31.51 |
| JN290817-4 | 17.7 | 1.43 | 2.39 | 0.00 | 2.73 | 0.153 | 7.892 | 32.30 |
| JN031017-2 | 14.63 | 1.01 | 2.12 | 0.00 | 2.77 | 0.156 | 9.393 | 30.08 |
| JN031017-3 | 10.64 | 0.80 | 2.13 | 0.00 | 2.80 | 0.155 | 11.273 | 27.80 |
| JN031017-4 | 10.64 | 0.64 | 2.14 | 0.00 | 2.81 | 0.152 | 13.153 | 29.54 |
| JN041017-7 | 15.81 | 1.05 | 2.13 | 0.32 | 2.81 | 0.151 | 9.395 | 31.66 |
| JN201217-3 | 20.81 | 1.51 | 2.12 | 0.160 | 2.71 | 0.15 | 2.635 | 30.10 |
| JN201217-6 | 20.98 | 1.53 | 2.19 | 0.00 | 2.75 | 0.15 | 2.632 | 30.23 |
| CS100317-1a | 4.07 | 0.29 | 0.29 | 0.35 | 0.00 | 0.00 | 0.188 | 5.188 |

Siloxane (PDMS) was weighed out into a glass beaker at 25° C. $TiO_2$ was added to the beaker containing PDMS and manually mixed for about 5 min to yield a milky-colored mixture. Aluminum powder was then added and manually mixed for about 5 minutes to yield a slightly grey mixture. CMC was added and manually mixed for about 5 minutes without yielding any changes in color or texture. $Ag_7NO_{11}$ powder was added and manually mixed for about 5 more minutes to yield a slightly more viscous and darker grey mixture. Half of the amount of silica was added and manually mixed until the silica appeared fully dispersed within the composition. The remaining half of silica was added and mix manually for about 10 minutes until the composition reached the desired viscosity and homogeneity.

The antimicrobial activities of the compositions were evaluated by exposing the composition to *Staphylococcus aureus* biofilms using same method described in Example 1. As shown in FIG. 2, an increase in anti-biofilm activity was achieved through an increase in the concentration of oxidizing agent silver oxynitrate in the composition (JN290817-1, 11 wt/wt % Ag; JN290817-2, 14 wt/wt % Ag; JN290817-3, 17 wt/wt % Ag; JN290817-4, 20 wt/wt % Ag; JN031017-2, 25 wt/wt % Ag; JN031017-3, 32 wt/wt % Ag; JN031017-4, 36 wt/wt % Ag). As shown in FIG. 3, incremental anti-biofilm activity was achieved through increasing PEG/PPG 18/18 dimethicone (PPD) composition within the composition, independent of PPD in isolation (JN031017-2, 25 wt/wt % Ag, 0 wt/wt % PPD; JN041017-7, 25 wt/wt % Ag, 1 wt/wt % PPD). As shown in FIG. 4, a significant increase in the anti-biofilm activity was obtained upon the inclusion of the oxidizing agent silver oxynitrate within the composition, with a further significant improvement upon the addition of PPD (JN201217-3, 7 wt/wt % Ag, 0.5 wt/wt % PPD; JN201217-6, 7 wt/wt % Ag, 0 wt/wt % PPD).

ADDITIONAL DISCLOSURES

The following are non-limiting, specific embodiments of the semi-solid composition and methods for preparing and using same:

Embodiment A. A composition comprising: a hydrophobic continuous phase comprising an oxidizing agent; and a disperse hydrophilic phase comprising at least one hydrophilic substance.

Embodiment B. The composition of Embodiment A, wherein the hydrophobic continuous phase comprises less than about 5 wt/wt % water, and exhibits an initial viscosity ranging from about 0 centipoise to about 1000 centipoise.

Embodiment C. The composition of Embodiment B, wherein the hydrophobic continuous phase comprises a polymeric compound selected from an aliphatic or silicone based short chain, or a polymeric compound selected from a lower alkane, higher alkane, liquid paraffin, paraffin wax, petrolatum, polydimethylsiloxane, polyalkylsiloxane, a dialkylsiloxane polymer, a dialkylsiloxane polymer comprising one or more polydimethylsiloxanes, or a combination thereof.

Embodiment D. The composition of Embodiment C, wherein the polymeric compound comprises polydimethylsiloxane exhibiting a viscosity ranging from about 5 centipoise to about 1,000 centipoise, and in an amount ranging from about 35 wt/wt % to about 80 wt/wt %.

Embodiment E. The composition of Embodiment C, wherein the hydrophobic continuous phase further comprises a non-aqueous solvent selected from dimethylsulfoxide, dichloromethane, tetrahydrofuran, or chloroform.

Embodiment F. The composition of Embodiment C, further comprising a secondary or ternary non-aqueous base in an amount ranging from about 1.0 wt/wt % to about 90 wt/wt %.

Embodiment G. The composition of Embodiment A, wherein the disperse hydrophilic phase comprises nanostructured silica selected from nano silica, fumed silica, or a combination thereof.

Embodiment H. The composition of Embodiment G, wherein the amount of nanostructured silica ranges from about 0.1 wt/wt % to about 30 wt/wt %, with a ratio of fumed silica to nano silica ranging from 1.0 to 0.1.

Embodiment I. The composition of Embodiment A, wherein the oxidizing agent exhibits a reduction potential greater than 0.0 V versus a standard hydrogen electrode.

Embodiment J. The composition of Embodiment I, wherein the oxidizing agent comprises a transition, lanthanide, or actinide metal having at least one metal element in an oxidized state greater than a metallic state.

Embodiment K. The composition of Embodiment I, wherein the metal element comprises silver, gold, copper, tin, titanium, zinc, iron, manganese, cobalt, platinum, nickel, cerium, or a combination thereof.

Embodiment L. The composition of Embodiment K, wherein the silver is in the form of Ag(II) or Ag(III) oxidation state or a combination thereof.

Embodiment M. The composition of Embodiment L, wherein the silver is selected from silver fluoride, silver bipyridine, silver carbamate, silver pyridinecarboxylic acid, a silver porphyrin, silver biguanide, a silver oxide comprising $AgO$, $Ag_2O_2$, $Ag_4O_4$, $Ag_2O_3$, $Ag_3O_4$, $Ag_7O_8X$, wherein X comprises $HCO_3^-$, $BF_4^-$, $CO_3^{2-}$, $NO_3^-$, $ClO_4^-$, $SO_4^{2-}$, or $F^-$, or a combination thereof.

Embodiment N. The composition of Embodiment M, wherein the silver comprises silver oxynitrate $Ag_7NO_{11}$.

Embodiment O. The composition of Embodiment K, wherein the concentration of silver ranges from about 0.1 wt/wt % to about 50 wt/wt %.

Embodiment P. The composition of Embodiment A, wherein the oxidizing agent comprises a metal, metal oxide or metal fluoride with or without counterions selected from a nitrate, carbonate, phosphate, sulfate, chloride, fluoride, tellurate, periodate, peroxide, perchlorate, permanganate, persulfate, borate, arsenate, or combinations thereof.

Embodiment Q. The composition of Embodiment P, wherein the metal compound is capable of forming bonds with a donor ligand selected from dithiocarbamate, aliphatic dithioloate, aromatic dithioloate, selenium ligand, sulfur ligand, ethylenediaminetetraacetic imine acid, ligand, oxime ligand, dimethylglyoxime, macrocylic amine, porphyrin, tetraazacyclohexadiene, pyridine, pyrazine, bipyridyl, phenanthroline, dimethylphosphine, dimethylarsine, dibutylthiourea, ethylenediimine, polypeptide, guanide, biguanide, polyguanide, phosphine, arsine, or a combination thereof.

Embodiment R. The composition of Embodiment A, wherein the oxidizing agent comprises a metalloid or a polyatomic non-metal.

Embodiment S. The composition of Embodiment G, further comprising a Pickering agent selected from a mineral, a clay, chitosan, cyclodextrin, starch, alginate, cellulose, or a combination thereof.

Embodiment T. The composition of Embodiment R, wherein the amount of the Pickering agent ranges from about 0.1 wt % to greater than about 15.0 wt %.

Embodiment U. The composition of Embodiment G, further comprising a surface-active agent selected from an alkyl sulfonate, alkyl quaternary ammonium, imide, imine, or a block co-polymer of an alkane, alkylsiloxane, ethylene glycol, vinyl pyrrolidone, vinyl alcohol, acrylic acid, phosphate, polyethylene glycol/polypropylene glycol dimethicone, cetyltrimethylammonium, or a combination thereof.

Embodiment V. The composition of Embodiment U, wherein the amount of the surface-active agent ranges from about 0.1 wt/wt % to about 10.0 wt/wt %.

Embodiment W. The composition of Embodiment G, further comprising a hydrogeling agent selected from a polymeric carbohydrate, saccharide, cellulose, acid, alcohol, pyrrolidone, bentonite, carbopol, carrageenan, xanthan gum, or a combination thereof.

Embodiment X. The composition of Embodiment W, wherein the hydrogeling agent comprises a water concentration of less than about 8.0 wt/wt %.

Embodiment Y. The composition of Embodiment X, wherein the amount of the hydrogeling agent ranges from about 0.1 wt/wt % to about 10.0 wt/wt %.

Embodiment Z. The composition of Embodiment G, further comprising an opacifying agent selected from titanium dioxide, zinc sulfate, zirconium oxide, zinc oxide, dolomite, barium sulfate, calcium carbonate, talc, or mica.

Embodiment AA. The composition of Embodiment Z, wherein the amount of the opacifying agent ranges from about 1.0 wt/wt % to about 10 wt/wt %.

Embodiment BB. The composition of Embodiment G, further comprising a masking agent selected from carbon black, pyrophyllite, alumina, aluminum, or bismuth oxychloride.

Embodiment CC. The composition of Embodiment BB, wherein the amount of the masking agent ranges from about 1.0 wt/wt % to about 10 wt/wt %.

Embodiment DD. A method for preparing the composition of Embodiment A, comprising the steps of:
mixing the hydrophobic continuous phase and the oxidizing agent to form a mixture; and
adding the disperse hydrophilic phase in portions to the mixture to form the composition.

Embodiment EE. The method of Embodiment DD, further comprising mixing one or more excipients selected from a Pickering agent, a surface-active agent, a hydrogeling agent, a hygroscopic agent, an opacifying agent, or a masking agent.

Embodiment FF. The method of Embodiment EE, wherein one or more components are mixed in the following sequence to form the mixture: the hydrophobic continuous phase, and one or more of an opacifying agent, a masking agent, a hydrogeling agent, and a surface-active agent.

Embodiment GG. The method of Embodiment FF, wherein the components comprise siloxane, titanium dioxide, aluminum powder, carboxymethyl cellulose, PEG/PPG dimethicone, and silver oxynitrate.

Embodiment HH. The method of Embodiment DD, conducted at ambient temperature ranging from 0° C. to 60° C.

Embodiment II. The method of Embodiment HH, conducted at ambient temperature ranging from 10° C. to 20° C.

Embodiment JJ. The method of Embodiment DD, wherein the components are mixed at 2000 RPM for about 5 minutes per component.

Embodiment KK. Use of the composition of any one of Embodiment A to Embodiment CC in the form of a semi-solid composition exhibiting antimicrobial or anti-inflammatory activity.

Additional embodiments which result from combining, integrating and/or omitting features of the embodiments explicitly described herein are not intended to be precluded.

The embodiments of the invention in which an exclusive property of privilege is claimed are defined as follows:

1. A semi-solid composition comprising:
   a hydrophobic continuous phase comprising an oxidizing agent comprising a metal in the form of metal (II) or metal (III) oxidation state or a combination thereof, and a non-aqueous solvent; and
   a disperse hydrophilic phase comprising nanostructured silica.

2. The composition of claim 1, wherein the hydrophobic continuous phase comprises less than about 5 wt/wt % water, and exhibits an initial viscosity ranging from about 0 centipoise to about 1000 centipoise.

3. The composition of claim 2, wherein the hydrophobic continuous phase comprises a compound selected from a lower alkane, higher alkane, liquid paraffin, paraffin wax, petrolatum, polydimethylsiloxane, or a combination thereof.

4. The composition of claim 3, wherein the compound comprises polydimethylsiloxane exhibiting a viscosity ranging from about 5 centipoise to about 1,000 centipoise, and in an amount ranging from about 35 wt/wt % to about 80 wt/wt %.

5. The composition of claim 1, wherein the non-aqueous solvent is selected from dimethylsulfoxide, dichloromethane, tetrahydrofuran, or chloroform.

6. The composition of claim 3, further comprising a secondary or ternary non-aqueous base in an amount ranging from about 1.0 wt/wt % to about 90 wt/wt %.

7. The composition of claim 1, wherein the nanostructured silica is selected from nano silica, fumed silica, or a combination thereof.

8. The composition of claim 7, wherein the amount of nanostructured silica ranges from about 0.1 wt/wt % to about 30 wt/wt %, with a ratio of fumed silica to nano silica ranging from 1.0 to 0.1.

9. The composition of claim 1, wherein the oxidizing agent exhibits a reduction potential greater than 0.0 V versus a standard hydrogen electrode.

10. The composition in claim 9, wherein the oxidizing agent comprises a transition, lanthanide, or actinide metal.

11. The composition of claim 9, wherein the metal comprises silver, gold, copper, tin, titanium, zinc, iron, manganese, cobalt, platinum, nickel, cerium, or a combination thereof.

12. The composition of claim 11, wherein the silver is in the form of Ag(II) or Ag(III) oxidation state or a combination thereof.

13. The composition of claim 12, wherein the silver is selected from silver fluoride, silver bipyridine, silver carbamate, silver pyridinecarboxylic acid, a silver porphyrin, silver biguanide, a silver oxide comprising AgO, $Ag_2O_2$, $Ag_4O_4$, $Ag_2O_3$, $Ag_3O_4$, $Ag_7O_8X$, wherein X comprises $HCO_3^-$, $BF_4^-$, $CO_3^{2-}$, $NO_3^-$, $ClO_4^-$, $SO_4^{2-}$, or $F^-$, or a combination thereof.

14. The composition of claim 13, wherein the silver comprises silver oxynitrate $Ag_7NO_{11}$.

15. The composition of claim 12, wherein the concentration of the silver ranges from about 0.1 wt/wt % to about 50 wt/wt %.

16. The composition of claim 1, wherein the oxidizing agent comprises a metal, metal oxide or metal fluoride with or without counterions selected from a nitrate, carbonate, phosphate, sulfate, chloride, fluoride, tellurate, periodate, peroxide, perchlorate, permanganate, persulfate, borate, arsenate, or combinations thereof.

17. The composition of claim 16, wherein the metal compound is capable of forming bonds with a donor ligand selected from dithiocarbamate, aliphatic dithioloate, aromatic dithioloate, selenium ligand, sulfur ligand, ethylenediaminetetraacetic acid, imine ligand, oxime ligand, dimethylglyoxime, macrocylic amine, porphyrin, tetraazacyclohexadiene, pyridine, pyrazine, bipyridyl, phenanthroline, dimethylphosphine, dimethylarsine, dibutylthiourea, ethylenediimine, polypeptide, guanide, biguanide, polyguanide, phosphine, arsine, or a combination thereof.

18. The composition of claim 1, wherein the oxidizing agent comprises a metalloid or a polyatomic non-metal.

19. The composition of claim 1, further comprising a Pickering agent selected from a mineral, a clay, chitosan, cyclodextrin, starch, alginate, cellulose, or a combination thereof.

20. The composition of claim 19, wherein the amount of the Pickering agent ranges from about 0.1 wt/wt % to greater than about 15.0 wt/wt %.

21. The composition of claim 1, further comprising a surface-active agent selected from an alkyl sulfonate, alkyl quaternary ammonium, alkane phosphate, a block co-polymer of an alkylsiloxane, ethylene glycol, vinyl pyrrolidone, vinyl alcohol, acrylic acid, or a combination thereof.

22. The composition of claim 21, wherein the amount of the surface-active agent ranges from about 0.1 wt/wt % to about 10.0 wt/wt %.

23. The composition of claim 1, further comprising a hydrogeling agent selected from a polymeric carbohydrate, saccharide, cellulose, acid, alcohol, pyrrolidone, bentonite, carbopol, carrageenan, xanthan gum, or a combination thereof.

24. The composition of claim 23, wherein the hydrogeling agent comprises a water concentration of less than about 8.0 wt/wt %.

25. The composition of claim 24, wherein the amount of the hydrogeling agent ranges from about 0.1 wt/wt % to about 10.0 wt/wt %.

26. The composition of claim 1, further comprising an opacifying agent selected from titanium dioxide, zinc sulfate, zirconium oxide, zinc oxide, dolomite, barium sulfate, calcium carbonate, talc, or mica.

27. The composition of claim 26, wherein the amount of the opacifying agent ranges from about 1.0 wt/wt % to about 10 wt/wt %.

28. The composition of claim 1, further comprising a masking agent selected from carbon black, pyrophyllite, alumina, aluminum, or bismuth oxychloride.

29. The composition of claim 28, wherein the amount of the masking agent ranges from about 1.0 wt/wt % to about 10 wt/wt %.

30. A method for preparing the composition of claim 1, comprising the steps of:
    mixing the hydrophobic continuous phase and the oxidizing agent to form a mixture; and
    adding the disperse hydrophilic phase in portions to the mixture to form the composition.

31. The method of claim 30, further comprising mixing one or more excipients selected from a Pickering agent, a surface-active agent, a hydrogeling agent, a hygroscopic agent, an opacifying agent, or a masking agent.

32. The method of claim 31, wherein one or more components are mixed in the following sequence to form the mixture: the hydrophobic continuous phase, and one or more of an opacifying agent, a masking agent, a hydrogeling agent, and a surface-active agent.

33. The method of claim 32, wherein the one or more components comprise siloxane, titanium dioxide, aluminum powder, carboxymethyl cellulose, PEG/PPG dimethicone, and silver oxynitrate.

34. The method of claim 30, conducted at ambient temperature ranging from 0° C. to 60° C.

35. The method of claim 34, conducted at ambient temperature ranging from 10° C. to 20° C.

36. The method of claim 30, wherein the components are mixed at 2000 RPM for about 5 minutes per component.

37. A semi-solid composition comprising:
    a hydrophobic continuous phase comprising silver oxynitrate $Ag_7NO_{11}$ inclusive of silver in the form of Ag(II) or Ag(III) oxidation state or a combination thereof, and a non-aqueous solvent; and a disperse hydrophilic phase comprising nanostructured silica;
    wherein the composition exhibits antimicrobial or anti-inflammatory activity.

38. The composition of claim 37, exhibiting antimicrobial activity against *Staphylococcus aureus* and *Pseudomonas aeruginosa*.

* * * * *